United States Patent [19]

Georges

[11] Patent Number: 4,574,795

[45] Date of Patent: Mar. 11, 1986

[54] COMPRESSION NAIL ASSEMBLY

[75] Inventor: Jawdat Georges, Kehl, Fed. Rep. of Germany

[73] Assignee: MECRON medizinische Produkte GmbH, Berlin, Fed. Rep. of Germany

[21] Appl. No.: 564,504

[22] Filed: Dec. 22, 1983

[30] Foreign Application Priority Data

Dec. 24, 1982 [DE] Fed. Rep. of Germany ... 8236698[U]

[51] Int. Cl.⁴ .............................................. A61F 5/04
[52] U.S. Cl. ............................. 128/92 BC; 128/92 R
[58] Field of Search .................. 128/92 A, 92 R, 69, 128/340, 84 R, 92 BC, 92 BA

[56] References Cited

U.S. PATENT DOCUMENTS

| | | | |
|---|---|---|---|
| 1,539,221 | 5/1925 | Tennant | 128/340 |
| 2,091,643 | 8/1937 | Longfellow | 128/84 R |
| 2,583,895 | 1/1952 | Siebrandt | 128/84 R |
| 2,614,559 | 10/1952 | Livingston | 128/92 BC |
| 4,212,294 | 7/1980 | Murphy | 128/92 BC |
| 4,275,717 | 6/1981 | Bolesky | 128/92 BC |
| 4,433,676 | 2/1984 | Bobechko | 128/69 |

OTHER PUBLICATIONS

DRI Industries catalog, pp. 11, 39, Bloomington, MN.
Machinery's Handbook, 20th Ed., p. 546, "Belleville Washers".

*Primary Examiner*—Gene Mancene
*Assistant Examiner*—C. W. Shedd
*Attorney, Agent, or Firm*—Spencer & Frank

[57] ABSTRACT

A compression nail assembly for engagement with an element fixed to a bone for placing bone parts on either side of a fracture in compression. The assembly includes a tightening sleeve and a tightening mandrel configured for insertion into the sleeve and having an end portion shaped in the form of a hook for engagement with the element.

4 Claims, 5 Drawing Figures

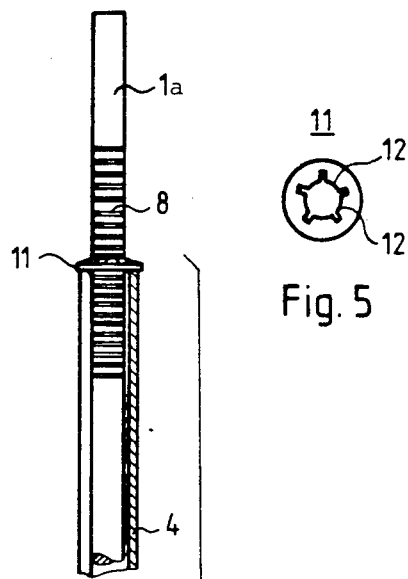
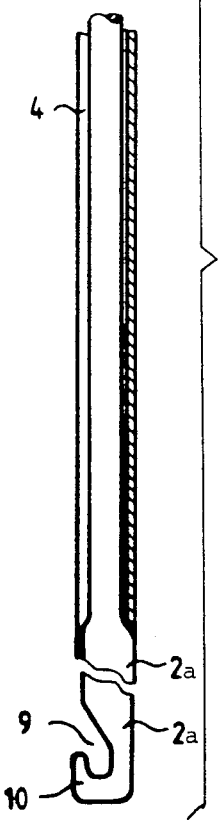
Fig. 5
Fig. 4

COMPRESSION NAIL ASSEMBLY

BACKGROUND OF THE INVENTION

The present invention relates to a compression nail assembly for engagement with an element fixed to a bone, such as a cotter pin, for placing bone parts on either side of a fracture in compression, and specifically to an assembly of the above type which includes a tightening sleeve and a tightening mandrel configured for insertion into the sleeve and having an end portion shaped for engaging the element fixed to the bone.

With a compression nail assembly of the above conventional type, known as a Kaessmann-nail, it is possible to realize stress-stable osteosynthesis of fractures and pseudarthrosis on long tubular bones. Its use has been developed on the basis of the Küntscher method, and in deviation from conventional marrow nail placement, is not based on the elastic tightening of the nail in an irregularly shaped marrow cavity. Rather, an optimum mechanical arrangement required for an undisturbed osteogenesis is achieved in the fracture gap with the Kaessmann compression nail placement, in that bone and metal implants, such as a tightening sleeve and a tightening mandrel, can be combined into a mutually clamped system by the use of measurable, interfragmentary pressure forces. Such a system remains essentially uninfluenced by external mechanical disturbance factors. The stability of a marrow nail osteosynthesis is thus increased many times.

In the known Kaessmann compression nail assembly, the tightening mandrel has an eyelet at one end. During implantation, it is necessary to pass an element, such as a cotter pin, through the bone and eyelet in order to secure the mandrel for subsequent tightening.

The manipulation required to implant this known compression nail is time consuming. The particular difficulty is to find the eyelet with the cotter pin as it is guided through the bone. The search for the eyelet with the cotter pin or with a drilling tool, respectively, is monitored through an image sensor. The instruments employed in the search for the eyelet interfere with the path of the X-rays of the image sensor and thus with the reproduction of the eyelet on the monitor screen of the image sensor.

SUMMARY OF THE INVENTION

It is therefore an object of the present invention to provide a compression nail assembly which eases the manipulation required for implantation.

The above and other objects are accomplished by the invention which provides for a compression nail assembly of the above type in which the tightening mandrel has an end portion in the shape of a hook for engaging an element (such as a cotter pin) attached to the bone.

The provision of a hook, instead of an eyelet, at the end of the mandrel, avoids the problem of the prior art mandrel with an eyelet in which a cumbersome search must be made for the eyelet with the cotter pin or a drilling tool provided for that purpose. Instead, with the compression nail assembly according to the invention, a search is made for the cotter pin with the hook. This has the advantage that to secure the mandrel to the cotter pin it is not necessary to perform manipulations at the cotter pin which cover up the region being imaged by the image sensor. Rather, manipulations take place remotely from the zone being imaged, at the free end of the tightening mandrel, where it can be gripped and rotated about its axis for engagement with the cotter pin as will be explained hereinafter.

BRIEF DESCRIPTION OF THE DRAWINGS

FIG. 4 is a partially sectional side elevational view of a compression nail assembly according to a preferred embodiment of the invention.

FIG. 5 is a top plan view of a component of the assembly illustrated in FIG. 4.

DESCRIPTION OF THE PRIOR ART STRUCTURE

Figures 1, 2, 3:
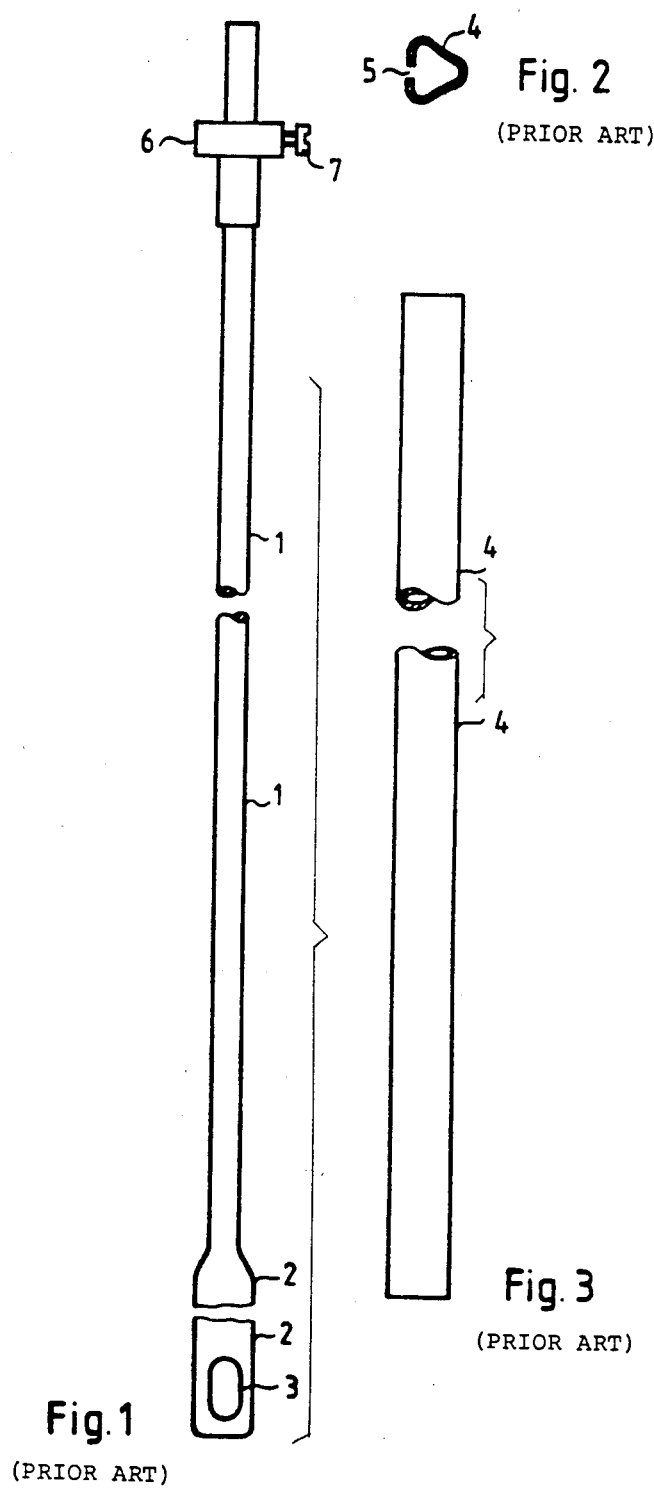
FIG. 1 is a side elevational view of components of a prior art compression nail assembly.
FIG. 2 is a cross-sectional view of a further component of the prior art construction.
FIG. 3 is a side elevational view of the component shown in FIG. 2.

FIG. 1 shows the known tightening mandrel 1 with a flattened end portion, or blade 2, which is provided with a cutout in the form of an eyelet 3.

FIGS. 2 and 3 show a longitudinally slotted tightening sleeve 4, for slidably receiving the mandrel 1. FIG. 3 shows a side view of the tightening sleeve 4 in a position associated with proper use of the tightening mandrel 1 of FIG. 1. FIG. 2 is a cross-sectional view of tightening sleeve 4 showing the longitudinal slot 5. When tightening mandrel 1 is inserted from the top (relative to FIG. 3) into sleeve 4, tightening mandrel blade 2 slides through slot 5. After insertion of mandrel 1 into sleeve 4, it is necessary, during the implantation of the compression nail, to introduce a Kirschner wire or a transverse screw through the bone and eyelet 3 to serve as cotter pin (not shown). Thereafter, tightening mandrel 1 is tensioned by a conventional tightening mechanism (not shown). Then, an arresting slider 6 is moved on the tightening mandrel 1 to the upper end of tightening sleeve 4 and is there clamped to the tightening mandrel 1 by means of a set screw 7.

As described above, this known compression nail assembly has the drawback that it is difficult to find the eyelet 3 with the cotter pin as it is guided through the bone. In searching for the eyelet 3 the manipulation of the cotter pin or drilling tool, respectively, interferes with the path of the X-rays of the image sensor and thus with the reproduction of the eyelet 3 on the screen of the image sensor monitor.

DESCRIPTION OF THE PREFERRED EMBODIMENT

FIG. 4 illustrates a compression nail assembly according to the invention which overcomes the foregoing problem.

In accordance with the invention, the end portion 2a has a cutout which forms a recess 9 which is partially enclosed by a hook 10. End portion 2a is flattened as in FIG. 1. With this configuration, the tightening mandrel 1a can be manipulated for securing the hook to the cotter pin rather than, as in the case of the prior art, manipulating the cotter pin to pass through the eyelet.

To implant the compression nail of the invention, the tightening mandrel 1a is initially introduced in the bone such that the plane of the end portion 2a is oriented in a direction parallel to the longitudinal direction of the cotter pin (not shown), with the hook 10 of the tightening mandrel 1a being initially brought past the cotter pin. Then the tightening mandrel 1a is gripped at its free end and rotated by 90° so that, upon being retracted, the hook 10 will engage the cotter pin. The manipulation of mandrel 1a to engage the hook 10 with the cotter pin is accomplished by monitoring the screen of the image sensor (not shown) which forms an X-ray image of the region of engagement of the hook with the cotter pin. Since the manipulation of the tightening mandrel 1a takes place at its free end, away from the region being imaged, the tools required for the manipulation do not cover up the region being imaged, as was the case with the known compression nail assembly wherein the manipulations had to be conducted at the cotter pin.

Moreover, the preferably flattened hook region offers an opportunity to initially guide the hook parallel and relatively close to the cotter pin. Thus, after the hook 10 is rotated by 90°, it rests against the cotter pin with a slight force and has the tendency to securely hook itself onto the cotter pin once the latter reaches the region of the recess 9 upon retraction of the tightening mandrel 1a.

Also referring now to FIG. 5, according to a preferred feature of the invention, a perforated disc 11 having a frustoconical shape with spring claws 12 oriented toward a central hole 13 is provided as the arresting means for tightening mandrel 1a. This arresting means is used in conjunction with knurling 8 on the tightening mandrel 1a along a length portion about a location which is spaced from the end portion 2a of the tightening mandrel 1a at a distance approximately corresponding, in the tensioned state, to the length of the tightening sleeve 4. This arresting means, compared to the slider 6 and set screw 7 shown in FIG. 1, reduces the manipulations required in the application of the compression assembly. It is noted that the disc 11 is not as easily releasable as the set screw of the prior art screw and slider. It is evident, however, that the simple releasability of the set screw, which constitutes an apparent advantage according to the prior art, is not necessary at all since the tightening mandrel is untensioned in any case by the removal of the cotter pin during removal of the implant.

It can be seen that the arrangement according to the present invention facilities manipulation of the compression nail assembly so that the intended fixing of a fracture can be performed faster and more easily. Due to the simplified manipulation, the stress on the patient from this operation is also reduced.

It will be understood that the above description of the present invention is susceptible to various modifications, changes and adaptations, and the same are intended to be comprehended within the meaning and range of equivalents of the appended claims.

What is claimed is:

1. A compression nail assembly for engagement with an element fixed to a bone for placing bone parts on either side of a fracture in compression, comprising:
   a tightening sleeve; and
   a tightening mandrel configured for insertion into said sleeve and having an end portion shaped in the form of a hook for engagement with the element.

2. A compression nail assembly as defined in claim 1, wherein said hook defines a plane and said end portion has flat surfaces parallel to said plane.

3. A compression nail assembly as defined in claim 1, further including a frustoconically shaped disc provided with an aperture for receiving said mandrel and having spring claws oriented toward the aperture for engaging and arresting said mandrel relative to said sleeve.

4. A compression nail assembly as defined in claim 3, wherein said sleeve has a length; further comprising a knurling provided on said mandrel along a length portion thereof; said length portior including a location which is, from said end portion, at a distance approximately equalling said length of said sleeve.

* * * * *